United States Patent [19]

Hacchow et al.

[11] Patent Number: 4,967,873
[45] Date of Patent: Nov. 6, 1990

[54] ACOUSTIC LENS APPARATUS

[75] Inventors: Masako Hacchow, Hachiooji; Takeshi Yamagishi, Sagamihara; Fumio Uchino, Hachiooji; Hiroshi Kajimura, Tokyo, all of Japan

[73] Assignee: Olympus Optical Co., Ltd.

[21] Appl. No.: 384,180

[22] Filed: Jul. 21, 1989

[30] Foreign Application Priority Data

Jul. 27, 1988 [JP] Japan ............................... 63-187822
Apr. 7, 1989 [JP] Japan .................................. 1-89187

[51] Int. Cl.$^5$ ........................................... G10K 11/30
[52] U.S. Cl. ................................................... 181/176
[58] Field of Search ............................... 181/176, 175

[56] References Cited

U.S. PATENT DOCUMENTS

| Re. 32,062 | 1/1986 | Samodovitz | 181/176 X |
| 3,687,219 | 8/1972 | Langlois | 181/176 |
| 3,903,990 | 9/1975 | Tannaka | 181/176 |
| 4,193,473 | 3/1980 | Hartmann | 181/176 |

FOREIGN PATENT DOCUMENTS

| 0150843 | 8/1985 | European Pat. Off. . |
| 2127657 | 4/1984 | United Kingdom . |
| 2139356 | 11/1984 | United Kingdom . |

Primary Examiner—Benjamin R. Fuller
Attorney, Agent, or Firm—Frishauf, Holtz, Goodman & Woodward

[57] ABSTRACT

In an acoustic lens apparatus of this invention, a lens surface formed on an ultarsonic medium has a longitudinal wave lens portion constituted by a first aspherical surface at its central area, and a transverse wave lens portion constituted by a second aspherical surface at its peripheral area. The ultrasonic medium includes a piezoelectric transducer for generating ultrasonic waves at its surface opposite to the lens surface. The ultrasonic medium is arranged so that the lens surface opposes a sample, a coupler medium is filled in the gap between the surface and the sample.

10 Claims, 6 Drawing Sheets

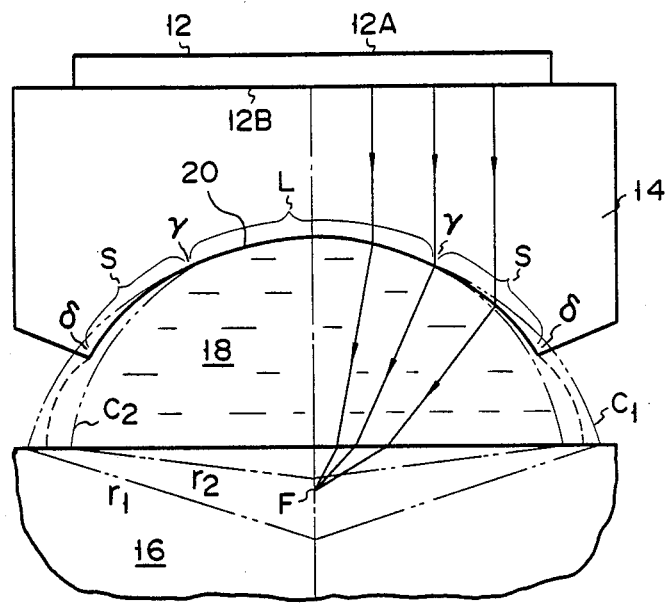
F I G. 1
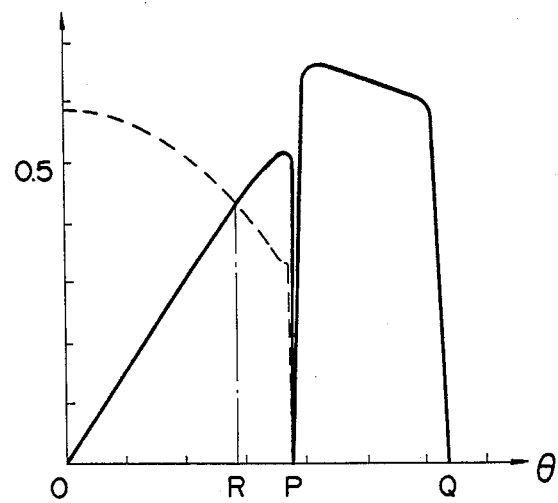
F I G. 2

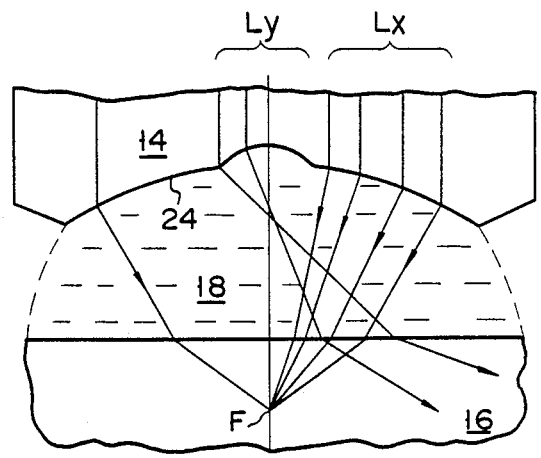
F I G. 5
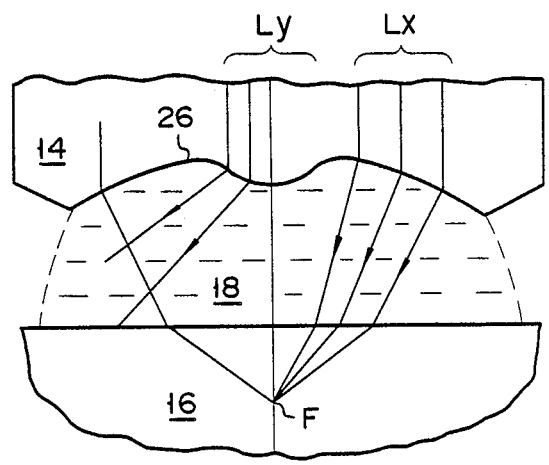
F I G. 6
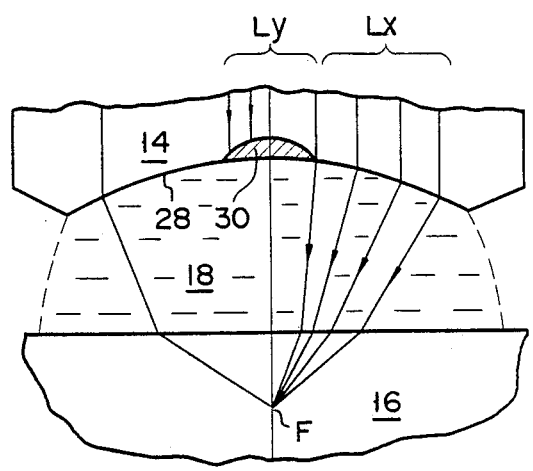
F I G. 7

4,967,873

ACOUSTIC LENS APPARATUS

BACKKGROUND OF THE INVENTION

1. Field of the Invention

The present invention relates to an acoustic lens apparatus for focusing ultrasonic waves and, more particularly, to an acoustic lens apparatus for focusing ultrasonic pulses, which is incorporated in an ultrasonic system such as a system for measuring the film thickness of a sample or a system for inspecting a sample nondestructively by radiating ultrasonic pulses onto the sample and detecting waves reflected by the sample, waves transmitted through the sample, or waves scattered by the sample.

2. Description of the Related Art

An acoustic lens generally includes a spherical surface formed on one surface of an ultrasonic medium for transmitting ultrasonic waves. This spherical surface opposes a sample, and a coupler medium is filled in the gap between this surface and the sample. As an ultrasonic medium, a substance such as sapphire and fused quartz, which has a relatively high propagation velocity of ultrasonic waves is mainly used. As a coupler medium, a liquid such as water having a relatively low propagation speed of ultrasonic waves is used. A piezoelectric transducer for generating ultrasonic waves is arranged on the other surface of the ultrasonic medium, which is opposite to the surface having the spherical surface formed thereon. Ultrasonic waves generated by the piezoelectric transducer propagate parallel to the axis of the lens (spherical surface) in the ultrasonic medium and are refracted by the spherical surface to be focused inside or at a surface of the sample. It is known that when a surface of a sample is to be observed by such an acoustic lens apparatus, a spherical aberration at the focal point of the lens is reduced to a negligible value, and a high resolution can be obtained.

When the inside of a sample is to be observed, ultrasonic waves refracted by the lens surface are caused to be incident on a surface of the sample before they are focused on one point, and are refracted at the interface between the coupler medium and the sample. At this time, ultrasonic waves near the peripheral portion of the sound flux are refracted at greater angles than those near the central portion of the sound flux. In addition, the ultrasonic waves incident on the sample are separated into longitudinal and transverse waves at the interface between the sample and the coupler medium, and are respectively refracted at different refraction angles. For this reason, the longitudinal and transverse waves propagate in the sample along different propagation paths. As a result, a plurality of focal points are dispersed in the sample, resulting in image blurring and degradation in resolution.

SUMMARY OF THE INVENTION

It is an object of the present invention to provide an acoustic lens which can obtain a high-resolution image by focusing ultrasonic pulses on a single point in a sample.

According to the present invention, there is provided an acoustic lens apparatus for inspecting a sample, comprising generating means for generating ultrasonic waves, and lens means made of an ultrasonic medium allowing ultrasonic waves to be transmitted therethrough, the lens means including a lens surface for focusing the ultrasonic waves, which are transmitted from the generating means through the ultrasonic medium, on a point in a sample, the lens surface being defined by first and second lens portions, and the first and second lens portions being formed by different aspherical surfaces.

BRIEF DESCRIPTION OF THE DRAWINGS

FIG. 1 is a sectional view of an acoustic lens apparatus according to a first embodiment of the present invention;

FIG. 2 is a graph showing an intensity distribution of longitudinal and transverse waves, which propagate in a sample after passing through the interface between the sample and the coupler medium, with respect to incident angles of ultrasonic waves at the interface;

FIG. 5 is a sectional view of an acoustic lens according to a third embodiment of the present invention;

FIG. 6 is a sectional view of an acoustic lens according to a fourth embodiment of the present invention;

FIG. 7 is a sectional view of an acoustic lens according to a fifth embodiment of the present invention;

DETAILED DESCRIPTION OF THE PREFERRED EMBODIMENTS

Figure 3:
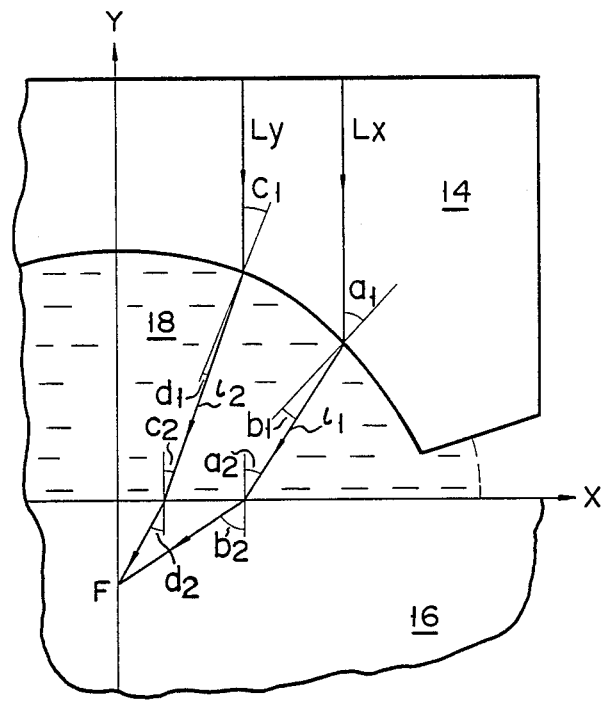
FIG. 3 is a sectional view for explaining the shape of a lens surface shown in FIG. 1.

A first embodiment of the present invention will be described below with reference to FIG. 1. FIG. 1 shows only the right half of propagation paths of ultrasonic waves, and the left half thereof is omitted.

A piezoelectric transducer 12 for generating ultrasonic waves is arranged in contact with one end face of an ultrasonic medium 14. The piezoelectric transducer 12 is constituted by a piezoelectric element having electrodes 12A and 12B formed on its upper and lower surfaces. When high-frequency pulses are applied to the electrodes 12A and 12B, the piezoelectric transducer 12 is excited to generate ultrasonic waves.

A lens surface 20 as an aspherical surface is formed on the surface of the ultrasonic medium 14, which is opposite to the surface on which the piezoelectric transducer 12 is arranged. A sample 16 is placed to oppose the lens surface 20, and a coupler medium 18 is interposed therebetween.

The lens surface 20 includes a longitudinal wave lens portion L for focusing longitudinal waves propagating in the sample 16 and a transverse wave lens portion S for focusing transverse waves propagating in the sample 16. The lens portion L defined by a boundary γ, is formed in a central area of the lens surface 20, whereas the lens portion S, defined by the boundary γ and an end portion δ, is formed on a peripheral area of the lens surface 20. Both the longitudinal and transverse lens portions L and S are aspherical surfaces. The lens portion L is formed by correcting a spherical surface $C_1$ having a radius $r_1$, and the lens portion S is formed by correcting a spherical surface $C_2$ having a radius $r_2$.

FIG. 2 shows an intensity distribution of longitudinal and transverse waves propagating in the sample 16 with respect to an incident angle θ. Referring to FIG. 2, a solid line represents an intensity distribution of a transverse wave, and a broken line represents an intensity distribution of a longitudinal wave. The intensity of a longitudinal wave has its peak at an angle of 0°, is reduced with an increase in the angle θ, and becomes substantially zero at an angle P or more. That is, no longitudinal waves propagate in the sample 16 with respect to an ultrasonic wave having an incident angle larger than the angle P. The intensity of a transverse wave is increased with an increase in incident angle, but is reduced near the angle P and temporarily becomes zero. As the incident angle is increased, the intensity of a transverse wave is increased again, and becomes zero at an angle Q or more. For this reason, with respect to an ultrasonic wave having a small incident angle, the ultrasonic waves propagating in the sample 16 are mostly longitudinal waves. With respect to an ultrasonic wave of an incident angle larger than the angle P, the ultrasonic waves propagating in the sample 16 are mostly transverse waves.

The lens surface 20 is formed on the basis of mathematical analysis so as to focus longitudinal and transverse waves propagating in the sample 16 on a single point. The lens surface 20 will be described below with reference to FIG. 3. Referring to FIG. 3, the lens axis is defined as the y-axis; and a sample surface perpendicular to the lens axis, as the x-axis. Both ultrasonic sound fluxes $L_x$ and $L_y$ generated by the piezoelectric transducer 12 propagate as longitudinal waves in the ultrasonic medium 14 so as to be parallel to the lens axis (y-axis). The sound flux $L_x$, which is incident on the lens surface 20 at an angle $a_1$, is refracted by the lens surface 20, emerges therefrom into the coupler medium 18, and is incident on the sample surface at an angle $a_2$. The sound flux $L_x$ is then refracted by the interface between the sample 16 and the coupler medium 18, and emerges therefrom into the sample 16 at an angle $b_2$. The sound flux $L_x$ propagating in the sample 16 is mostly constituted by transverse waves. The sound flux $L_y$ is incident on the lens surface 20 at an angle $c_1$ and emerges therefrom into the coupler medium 18 at an angle $d_1$. The sound flux $L_y$ is then incident on the sample surface at an angle $c_2$ and emerges therefrom into the sample $d_2$ at an angle $d_2$. The sound flux $L_y$ propagating in the sample 16 is mostly constituted by longitudinal waves.

If the sound velocities of the sound flux $L_y$ in the ultrasonic medium 14, the coupler medium 18, and the sample 16 are respectively represented by $V_L$, $V_C$, and $V_S$, the following equations can be established according to the Snell's Laws:

$\sin a_2 / \sin b_2 = V_C / V_S$ ... (1)
$\sin a_1 / \sin b_1 = V_L / V_C$ ... (2)

Since the sound flux $L_y$ propagates parallel to the lens axis in the ultrasonic medium 14, $b_1 + a_2 = a_1$ ... (3)

Therefore, $a_2 = \sin^{-1}\{(V_c \sin b_2)/V_S\}$ ... (4)

can be established on the basis of equation (1), and $\sin a_1 = V_L \sin (a_1 - a_2)/V_C$ ... (5)

can be obtained on the basis of equations (2) and (3).

Table 1 shows the critical angles of an ultrasonic wave whose sound velocity in water is 1,500 m/s with respect to various substances, and sound velocities of the ultrasonic wave in these substances. Although the sound velocity in ceramic varies depending on each ceramic product, generally used values are shown.

TABLE 1

| Substance | Longitudinal Wave | | Transverse Wave | |
| --- | --- | --- | --- | --- |
| | Sound Velocity (m/s) | Critical Angle (°) | Sound Velocity (m/s) | Critical Angle (°) |
| ceramic | (10,000) | 8.26 | (6,000) | 14.48 |
| fused quartz | 5,968 | 14.56 | 3,764 | 23.49 |
| silicon | 8,433 | 10.25 | 5,843 | 14.88 |
| iron | 5,010 | 17.42 | 2,270 | 41.36 |
| polystyrene | 2,350 | 39.67 | 1,120 | — |

It is assumed here that fused quartz, water, and silicon are used as the materials of the ultrasonic medium 14, the coupler medium 18, and the sample 16, respectively the velocity $V_L$ in the fused quartz is 5,986 m/s; the velocity $V_C$ isn the water is 1,500 m/s; and the velocity $V_S$ in the silicon is 5,843 m/s.

If $b_2 = 60°$, $a_2 = 12.84°$ from equation (4).
According to equation (5), $$\sin a_1 = 3.88\{\sin a_1 \cdot \cos(12.84°) - \cos a_1 \cdot \sin(12.84°)\}$$

$$= 3.88 \sin a_1 - 0.88 \sqrt{1 - \sin^2 a_1}$$

$$2.88 \sin a_1 = 0.88 \sqrt{1 - \sin^2 a_1}$$

$$3.27 \sin a_1 = \sqrt{1 - \sin^2 a_1}$$

$$10.69 \sin^2 a_1 = 1 - \sin^2 a_1$$

$$\sin^2 a_1 = 0.085$$

$$a_1 = 17.0$$

$$b_1 = (17.0 - 12.84)°$$

$$= 4.16°$$

Therefore, $a_1 = 17.0°$, $b_1 = 4.16°$, $a_2 = 12.84°$, and $b_2 = 60°$ can be obtained.

Calculations similar to those described above are also performed for the sound flux $L_y$. More specifically, since the sound velocities $V_L$ and $V_C$ in the fused quartz and in the water are respectively given as $V_L = 5,986$ m/s and $V_C = 1,500$ m/s as with the case of the sound flux $L_x$, and the sound velocity $V_{SO}$ in the silicon is given as $V_S = 8,433$ m/s, if $d_2 = 30°$, $c_1 = 5.10°$, $d_1 = 6.54°$, $c_2 = 1.44°$, and $d_2 = 30°$ are obtained according to equations (3), (4), and (5).

The above calculations are performed for the sound flux $L_x$ while the angle $b_2$ is changed, thus obtaining the values of angle $a_1$ with respect to various values of the angle $b_2$. Similarly, the above calculations are performed for the sound flux $L_y$ while the angle $d_2$ is changed, thus obtaining the values of the angle $c_1$ with respect to various values of the angle $d_2$. The lens surface 20 for focusing both the sound fluxes $L_x$ and $L_y$ on a point F is determined on the basis of these angles $b_2$, $a_1$, $d_2$, and $c_1$.

The sound flux $L_x$ to be focused on a point F is incident on the interface between the coupler medium 18 and the sample 16 at the incident angle $a_2$, and is refracted at the refraction angle $b_2$. The sound flux $L_x$, which is incident on the interface between the coupler medium 18 and the sample 16 at the incident angle $a_2$, is incident on the lens surface 20 at the incident angle $a_9$, and is refracted at the refraction angle $b_1$. Similarly, the sound flux $L_y$ to be focused on the point F is incident on the interface between the coupler medium 18 and the sample 16 at the angle $c_2$, and is refracted at the angle $d_2$. The sound flux $L_y$, which is incident on the interface between the coupler medium 18 and the sample 16 at the incident angle $c_2$, is incident on the lens surface 20 at the incident angle $c_1$, and is refracted at the refraction angle $d_1$. Therefore, the transverse wave lens portion S of the lens surface 20 is formed by a curved surface allowing the sound flux $L_x$, which propagates parallel to the y-axis, to have the incident angle al and the refraction angle $b_1$ on a propagation path 11 of the sound flux $L_x$ in the coupler medium 18. The longitudinal wave lens portion L of the lens surface 20 is formed by a curved surface alowing the sound flux $L_y$, which propagates parallel to the y-axis, to have the incident angle $c_1$ and the refraction angle $d_1$ on a propagation path 12 of the sound flux $L_x$ in the coupler medium 18. That is, the spherical surface $C_1$ is corrected to allow the sound flux $L_x$ to have the incident angle $a_1$ and the refraction angle $b_{10}$ and the spherical surface $C_2$ is corrected to allow the sound flux $L_y$ to have the incident angle $c_1$ and the refraction angle $d_1$.

At this time, the boundary $\gamma$ between the lens portions L and S is properly determined with reference to FIG. 2. For example, the boundary $\gamma$ is set at a position on the lens surface 20 at which a sound flux is incident at an incident angle R, at which longitudinal and transverse waves in the sample 16 have the same intensity. In addltion, the end portion $\delta$ of the lens surface 20 is properly determined in consideration of the distance from the focal point to the sample surface.

Parallel sound fluxes generated by the piezoelectrie transducer 12 propagate parallel to the lens axis in the ultrasonic medium 14. The parallel sound fluxes are refracted by the lens surface 20, and are focused onto a large number of imaginary focal points in the coupler medium 14. The sound fluxes which are incident on the surface of the sample 16 are further refracted by the interface between the coupler medium 18 and the sample 16. As a result, both the sound fluxes $L_x$ and $L_y$ are focused on the point F in the sample 16. If any object to be inspected, such as a damage or defect, is present at the point F, the ultrasonic waves, which are focused on the point F, are reflected or scattered at the point F. Most of the reflected ultrasonic waves are refracted by the interface between the sample 16 and the coupler medium 18 and by the lens surface 20 to become parallel sound fluxes, which propagate in the ultrasonic medium 14 and return to the piezoelectric transducer 12. The ultrasonic waves which reach the transducer 12 are converted into electric signals to be detected.

Figure 4:
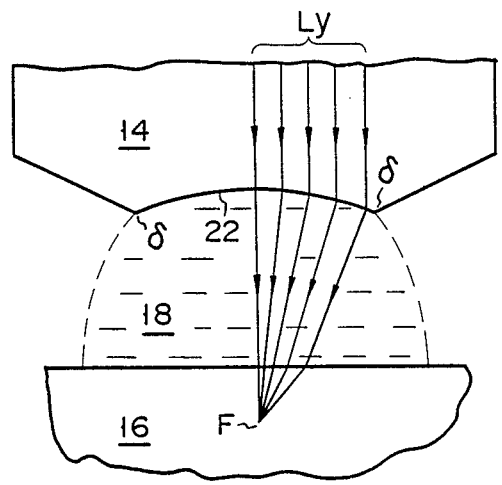
FIG. 4 is a sectional view of an acoustic lens according to a second embodiment of the present invention.

A second embodiment of the present invention will be described below with reference to FIG. 4. A lens surface 22 of this embodiment is constituted by only the longitudinal wave lens portion L described in the first embodiment. Therefore, when ultrasonic waves are incident on a sample 16, only longitudinal waves propagate in the sample 16 and are focused on a point F in the same manner as described in the first embodiment. In this embodiment, since only longitudinal waves propagate in the sample 16, high-precision inspection data free from the influences of transverse waves can be obtained.

A third embodiment of the present invention will be described below with reference to FIG. 5. A lens surface 24 is designed such that its central portion is formed into a concave surface having a curvature sufficiently larger than that of the longitudinal wave lens portion L described in the first embodiment, and its peripheral portion is constituted by the transverse wave lens portion S described in the first embodiment.

Sound fluxes $L_x$ which are incident on the peripheral area of the lens surface 24 are focused on a single point F in a sample, as described above. Sound fluxes $L_y$ which are incident on the central area of the lens surface 24 are refracted by the lens surface 24, are focused in a coupler medium 18 once, and are incident on the sample 16 as divergent sound fluxes. The sound fluxes $L_y$ incident on the sample 16 are refracted by the interface between the coupler medium 18 and the sample 16 so as to further diverge. That is, the sound fluxes $L_y$ which are incident on the central portion of the lens surface 24 are converted into divergent sound fluxes, and propagate in the sample 16. As a result, only the sound fluxes $L_x$ which are incident on the peripheral area of the lens surface 24 are focused on the point F in the sample 16.

A fourth embodiment of the present invention will be described below with reference to FIG. 6. A lens surface 26 is designed such that its lens central area, on which sound fluxes $L_y$ are incident, is formed into a convex surface, and its lens peripheral area, on which sound fluxes $L_x$ are incident, is constituted by the transverse wave lens portion S described in the first embodiment.

Sound fluxes $L_y$, which are incident on the central area of the lens surface 26, i.e., the convex surface portion, are refracted by the surface of the convex surface portion and are converted into divergent sound fluxes. Sound fluxes $L_x$, which are incident on the peripheral area of the lens surface 26, are focused on a point F in a sample 16, as described in the first embodiment.

In this embodiment, only the sound fluxes $L_x$ are used to observe the sample 16. In addition, since the sound fluxes $L_y$ are diverged by the convex surface portion, the level of reflected waves as stray sounds can be reduced.

An acoustic lens according to a fifth embodiment of the present invention will be described below with reference to FIG. 7. A lens surface 28 includes a sound absorbing member 30 at its central portion and a peripheral area constituted by the transverse wave lens portion S described in the first embodiment.

Sound fluxes $L_y$, which are incident on the central portion of the lens surface 28, are absorbed by the sound absorbing member 30, and hence are not output into a coupler medium 18. Therefore, only sound fluxes $L_x$, which are incident on the peripheral area of the lens surface 28, are focused on point F in a sample.

Figure 8:
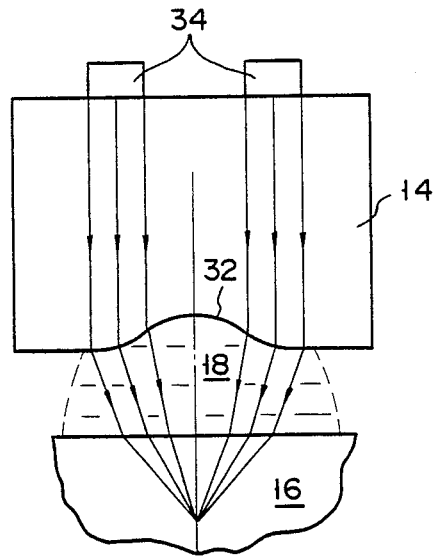
FIG. 8 is a sectional view of an acoustic lens according to a sixth embodiment of the present invention.

A sixth embodiment of the present invention w 11 be described below with reference to FIG. 8. In this embodiment, a peripheral area of a lens surface 32 is constituted by the transverse wave lens portion S described in the first embodiment. A piezoelectric transducer 34 is arranged on the surface of an ultrasonic medium 14, which is opposite to the lens surface 32, at only the area corresponding to the lens portion S.

With this arrangement, ultrasonic waves generated by the piezoelectric transducer 34 are refracted by the lens surface 32, and only transverse waves are focused in a sample 16. Since no ultrasonic wave is incident on the central portion of the lens surface, the central portion can be formed into any shape.

Figure 9:
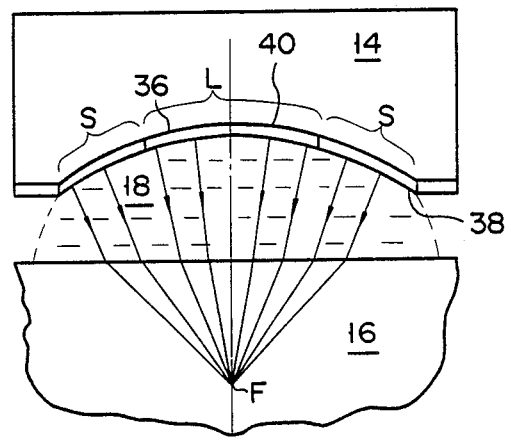
FIG. 9 is a sectional view of an acoustic lens according to a seventh embodiment of the present invention.

A seventh embodiment of the present invention will be described below with reference to FIG. 9. A piezoelectric transducer 36 is arranged at a central portion of an aspherical surface 40 formed on an ultrasonic medium 14, and a piezoelectric transducer 38 is arranged on a peripheral portion of the aspherical surface 40. In this embodiment, a lens surface defined by a interface between the piezotransducers 36, 38 and the aspherical surface 40. The aspherical surface 40 is designed such that ultrasonic waves generated by the piezoelectric transducers 36 and 38 are caused to propagate along the propagation paths shown in the first embodiment. That is, the aspherical surface 40 is formed by a curved surface which is perpendicular to the propagation paths of sound fluxes $L_x$ and $L_y$ in a coupler medium 18. Longitudinal and transverse waves generated by the transducers 36 and 38 are directly radiated onto the coupler medium 18 and are focused on a point F in a sample 16 through the same propagation paths as in the first embodiment.

Figure 10:
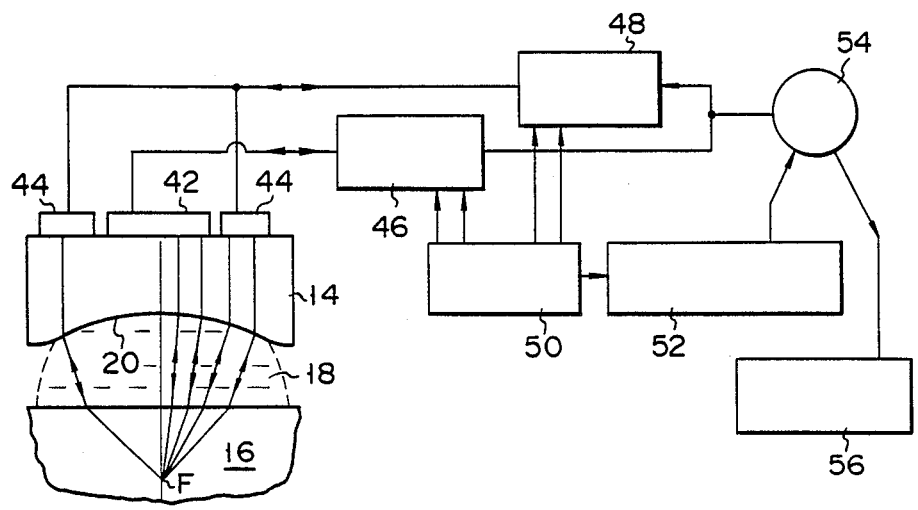
FIG. 10 is a block diagram of an acoustic lens apparatus according to an eighth embodiment of the present invention.

An acoustic lens apparatus according to an eighth embodiment of the present invention will be described below with reference to FIG. 10. In this embodiment, similar to the first embodiment, an ultrasonic medium 14 includes a lens surface 20 having a longitudinal wave lens portion L formed in its central area and a transverse wave lens portion S formed in its peripheral area. A first piezoelectric transducer 42 for generating ultrasonic pulses propagating in the longitudinal lens portion L is arranged at the central portion of the surface of the ultrasonic medium 1 which is opposite to the lens surface 20. A second piezoelectric transducer 44 for generating ultrasonic pulses propagating in the transverse wave lens portion S is arranged around the first piezoelectric transducer 42. The first piezoelectric transducer 42 is connected to a gate circuit 46 for permitting passage of a pulse generated by a pulse signal generator 52 at a predetermined timing. The second piezoelectric transducer 44 is connected to a gate circuit 48 for permitting passage of a pulse generated by the pulse signal generator 52 at a predetermined timing. The gate circuits 46 and 48 are connected to a timing circuit 50. The pulse signal generator 52 is connected to the timing circuit 50 and a circulator 54 for supplying a series of pulses generated by the pulse signal generator 52 to the respective transducers 42 and 44. The circulator 54 is connected to a receiver 56 for receiving and processing reflection signals from a sample 16. The timing circuit 50 generates control signals for controlling the gate circuits 46 and 48, the pulse signal generator 52, and the receiver 56 in a predetermined sequence in accordance with data such as the focal length of a lens and the sound velocities of ultrasonic waves in a coupler medium and a sample.

FIG. 11a shows timing charts of signals obtained by removing noise, such as primary reflection signals from a lens surface and reflection signals from a sample surface, from reflection signals.

Figure 11:
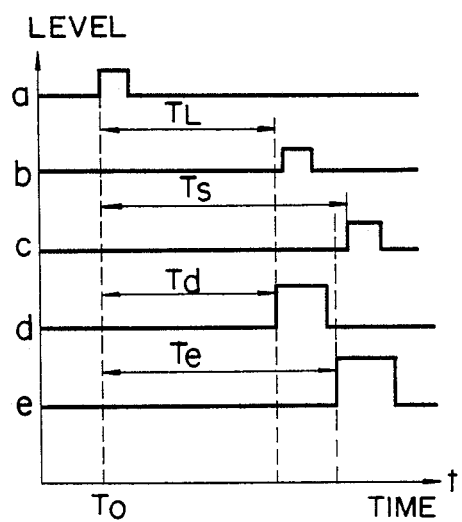
FIG. 11A shows timing charts of respective components of the apparatus in FIG. 10.

In response to a timing signal from the timing circuit 50, the pulse signal generator 52 generates a pulse shown by a in FIG. 11 and at the same time the gates circuits 46 and 48 are enabled. As a result, the pulse signal is supplied through gate circuits 46 and 48 to the respective transducers 42 and 44 through the circulator 54. Parallel sound fluxes of ultrasonic waves generated by the transducers 42 and 44 propagate parallel to the lens axis, and are refracted by the lens surface 20. The parallel sound fluxes are then converted into converging sound fluxes and propagate in the coupler medium 18. The converging sound fluxes are refracted by the interface between the coupler medium 18 and the sample 16. Most of the sound fluxes generated by the first piezoelectric transducer 42 and propagating in the sample 16 are longitudinal waves, whereas most of the sound fluxes generated by the second piezoelectric transducer 44 and propagating in the sample 16 are transverse waves. Both the longitudinal and transverse waves are focused on a single point F in the sample 16. The longitudinal and transverse waves which are scattered at the point F respectively return to the first and second piezoelectric transducers 42 and 44 along the incident propagation paths and are converted into electric signals by the transducers 42 and 44.

The sound waves are received by the transducers 42 and 44 with delays corresponding to time intervals TL and Ts with respect to the pulse (shown in a of FIG. 11) generated by the pulse signal generator 52, as shown by a and c in FIG. 11. The timing circuit 50 supplies a gate signal (d) which rises at a timing Td before the end of the time interval TL to the gate circuit 46, and supplies a gate signal (e) which rises at a timing Te before the end of the time interval TL to the gate circuit 48. With this operation, the gate circuits 46 and 48 are respectively enabled at predetermined timings, and the pulses, which were converted into electrical signals by the first and second piezoelectric transducers 42 and 44, are supplied to the receiver 56 through the circulator 54. The receiver 56 processes the two reception pulses as signals supplied from a single point in the sample 16.

Figure 12:
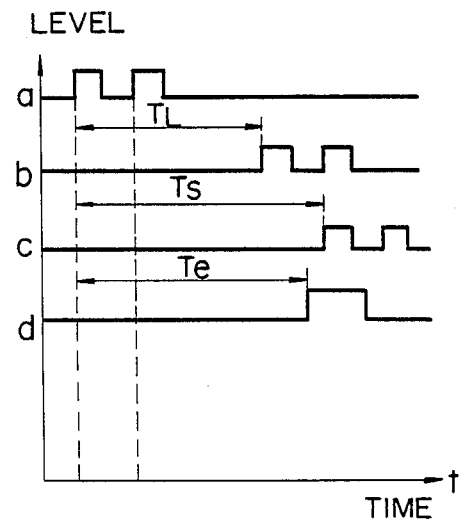
FIG. 12 shows timing charts of the apparatus in FIG. 10 in another sequence control.

Control in another sequence will be described below with reference to FIG. 12. As shown in by a in FIG. 12, after a first pulse is generated, a seeond pulse is generated by the pulse generating circuit 52 with a delay corresponding to a time interval (Ts—TL), and at the same time the gate circuits 46 and 48 are enabled. As a result, the two pulses are supplied to the respective transducers 42 and 44 through the circulator 54.

Ultrasonic waves generated by the first piezoelectric transducer 42 are converted into longitudinal waves at the interface between the coupler medium 18 and the sample 16 and are focused on the point F in the sample 16. Ultrasonic waves generated by the second piezoelectric transducer 44 are converted into transverse waves at the interface between the coupler medium 18 and the sample 16 and are focused on the point F in the sample 16. If an object to be inspected is present at the point F in the sample 16, the ultrasonic waves focused on the focal point F are reflected or scattered. The ultrasonic waves reflected or scattered at the focal point are fed back to the transducers 42 and 4 along the propagation paths so as to be converted into reception pulses. At this time, the second pulse of the reception pulses received by the first piezoelectric transducer 42 is synchronized with the first pulse received by the second piezoelectric transducer 44. b and c in FIG. 12 show this state. The timing circuit 50 supplies a gate signal to the gate circuits 46 and 48 at a timing Te shown by d in FIG. 12 so that the gate circuits 46 and 48 are xept enabled for a predetermined period of time. That is, the gate circuits 46 and 48 are enabled before the arrival of the second pulse after the arrival of the first pulse received by the first piezoelectric transducer 42, and are disabled before the arrival of the second pulse after the arrival of the first pulse received by the second piezoelectric transducer 44. As a result, the second pulse received by the transducer 42 passes through the gate circuit 46, and the first pulse received by the second transducer 44 passes through the gate circuit 48. The two pulses passing through the gate circuits 46 and 48 are supplied to the receiver 56 through the circulator 54 and are processed thereby.

In this embodiment, the distance between the first and second piezoelectric transducers 42 and 44 may be increased to prevent reception and transmission of sound waves in an area in the sample 16 where both longitudinal and transverse waves are present, e.g., an area which corresponds to the interval between R and P in FIG. 2.

Figure 13:
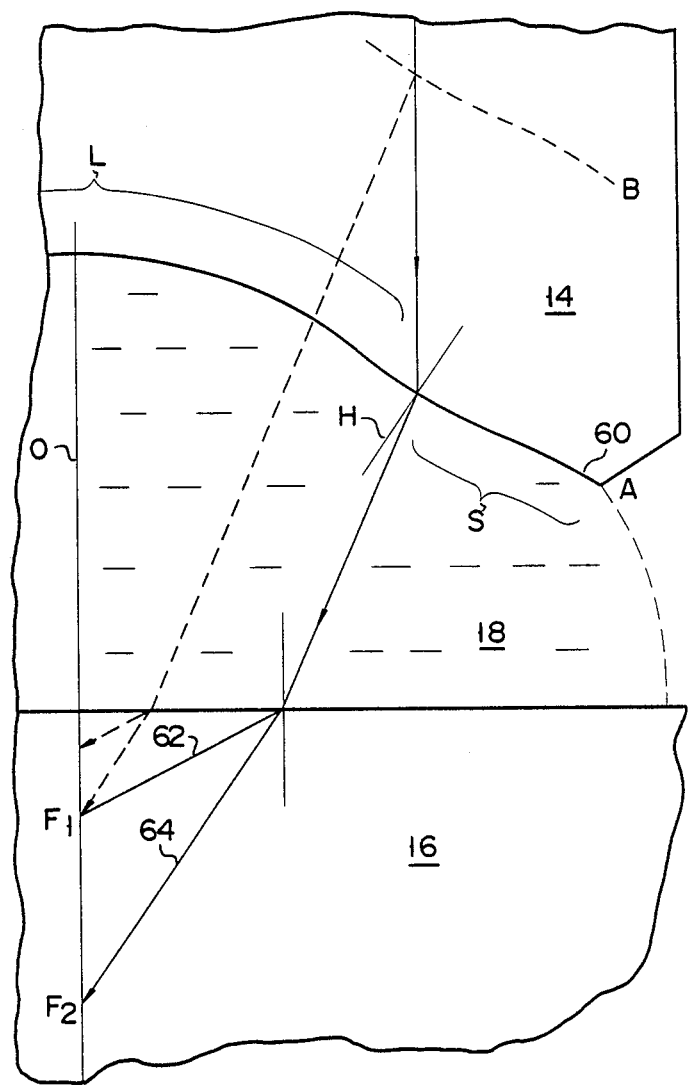
FIG. 13 is a sectional view for explaining a lens surface according to a ninth embodiment of the present invention.

A ninth embodiment of the present invention will be described below with reference to FIG. 13. A lens surface 60 includes longitudinal and transverse wave lens portions L and S. The longitudinal lens portion L is formed by first aspherical surface through which parallel sound fluxes incident on a central area of the lens surface 60 are focused on a point $F_1$ in a sample 16. The transverse lens portion S is formed as a second aspherical surface through which parallel sound fluxes incident on a peripheral area of the lens surface 60 are focused on a point $F_2$ below the point $F_1$. The longitudinal and transverse lens portions L and S are connected to each other such that normal lines H to the lens portions L and S coincide with each other at the boundary thereof. As a result, the lens surface 60 has a smooth continuous inclination. With this arrangement, a lens can be very easily processed.

In this embodiment, the focal points $F_1$ and $F_2$ of the longitudinal and transverse lens portions L and S are independently present in the sample 16. Therefore, when the sample 16 is to be observed, either of the focal points $F_1$ and $F_2$ is selected as an observation point.

Observation of the inside of the sample at the focal point $F_1$ will be described with reference to FIG. 13. Parallel sound fluxes of ultrasonic waves generated by a piezoelectric transducer (not shown) are refracted by the lens surface 60 and converted into focused sound fluxes. The focused sound fluxes propagate in a coupler medium 18 and are refracted by the interface between the coupler medium 18 and the sample 16. Of the ultrasonic waves incident on the sample 16, sound fluxes propagating in the sample 16 as longitudinal waves are focused on the point $F_1$. If an object to be inspected is present at the point $F_1$, the sound fluxes focused on the point $F_1$ are reflected or scattered. The reflected or scattered sound fluxes pass through the longitudinal lens portion L to be converted into parallel sound fluxes, and return to the piezoelectric transducer. Sound fluxes propagating in the sample 16 as transverse waves are focused on the point $F_2$. If an object to be inspected is present at the point $F_2$, the sound fluxes are reflected or scattered. The reflected or scattered sound fluxes are refracted by the transverse wave lens portion S to be converted into parallel sound fluxes, and return to the piezoelectric transducer.

The timings of a sound flux (longitudinal sound flux) propagating in the sample 16 as a longitudinal wave and a sound flux (transverse sound flux) propagating in the sample 16 as a transverse wave will be compared. As is apparent from FIG. 13, a propagation path 62 of the longitudinal sound flux is shorter than a propagation path 64 of the transverse sound flux. In addition, the propagation velocity of the longitudinal sound flux is higher than that of the transverse sound flux in the sample 16. Therefore, the longitudinal sound flux returns to the piezoelectric transducer earlier than the transverse sound flux. When reflected or scattered waves are to be detected, only the longitudinal sound flux is used as observation data by using a time gate on the basis of the difference in arrival time at the piezoelectric transducer between the longitudinal and transverse sound fluxes.

When the same point is to be observed by using the transverse sound flux, the lens surface 60 is set at a position B so as to focus the transverse sound flux, which is refracted by the lens portion S, on the point $F_1$. In this case, detection of reflected or scattered waves is performed by using a time gate which is set at a timing at which the transverse sound flux returns, and only the transverse sound flux is used as data to be detected.

In this embodiment, observation is performed by using one of longitudinal and transverse sound fluxes. The position of the lens surface 60 and a gate timing are determined in accordance with the type of sound flux to be used. Since one of separated longitudinal and transverse sound fluxes is used for observation, noise due to the other sound flux is reduced, and good observation can be performed.

According to a tenth embodiment of the present invention, a lens surface of an acoustic lens includes longitudinal and transverse lens portions L and S. The lens surface is designed such that the incident angle of a sound flux passing through the boundary of the lens portions L and S is smaller than the critical angle upon incidence of the sound flux.

When a sound flux is incident on a surface of a sample at the critical angle, a surface elastic wave is excited at the surface. After this surface elastic wave propagates on the surface by a predetermined distance, the wave emerges from the surface as if it returned from the focal point of the lens. When the inside of a sample is to be observed, such a surface elastic wave causes noise.

In this embodiment, a sound wave passing through the boundary of the lens portions L and S is set to be incident on a surface of a sample at an incident angle smaller than the critical angle. Therefore, no surface elastic wave is generated on the surface of the sample, and a sound flux can be effectively transmitted to an observation point.

When this embodiment is to be applied to the abovedescribed ninth embodiment, if the incident angle with respect to a surface of a sample is set to be considerably smaller than the critical angle, e.g., the portion L can be reduced in size, and the transverse wave lens portion S can be increased in size. As a result, an aspherical surface lens having a high output ratio of longitudinal and transverse waves can be provided.

What is claimed is:

1. An acoustic lens apparatus for inspecting a sample, comprising:
    means for generating an ultrasonic wave flux which is applied to the sample, to provide longitudinal and transverse ultrasonic waves which travel in the sample; and
    lens means made of a medium allowing said ultrasonic wave flux to be transmitted therethrough, said lens means including a lens surface having first and second lens portions coupled to each other with a boundary therebetween, said first lens portion being arranged for focusing said longitudinal ultrasonic waves on a point in the sample, and said second lens portion being arranged for focusing said transverse ultrasonic waves on said point, said first and said second lens portions being formed by different aspherical surfaces.

2. An apparatus according to claim 1, wherein said generating means comprises a piezoelectric transducer.

3. An apparatus according to claim 2, wherein said lens means is defined by an interface between the piezoelectric transducer and the medium.

4. An apparatus according to claim 1, wherein said generating means comprises a first piezoelectric transducer for generating an ultrasonic wave flux to be transmitted to said first lens portion, and a second piezoelectric transducer for generating an ultrasonic wave flux to be transmitted to said second lens portion.

5. An apparatus according to claim 1, wherein portions of said ultrasonic wave flux which pass through said first lens portion are incident upon a surface of the sample at an angle smaller than a critical angle which is an uppermost limit for the wave flux portions to provide the longitudinal ultrasonic wave in the sample.

6. An acoustic lens apparatus for inspecting a sample, comprising:
   means for generating an ultrasonic wave flux which is applied to the sample, to provide longitudinal and transverse ultrasonic waves which travel in the sample; and
   lens means made of an ultrasonic medium allowing said ultrasonic wave flux to be transmitted therethrough, said lens means including a lens surface having first and second lens portions coupled to each other with a boundary therebetween, said first lens portion being arranged for focusing said longitudinal ultrasonic waves on a first point in the sample, and said second lens portion being arranged for focusing said transverse ultrasonic waves on a second point other than said first point, said first and said second lens portion being formed by different aspherical surfaces.

7. An apparatus according to claim 6, wherein a normal line to the aspherical surface constituting said first lens portion coincides with a normal line to the aspherical surface constituting said second lens portion at said boundary at which said first and second lens portions are connected.

8. An apparatus according to claim 6, wherein portions of said ultrasonic wave flux which pass through said first lens portion are incident upon a surface of the sample at an angle smaller than a critical angle which is an uppermost limit for the wave flux portions to provide the longitudinal ultrasonic wave in the sample.

9. An acoustic lens apparatus for inspecting a sample, comprising:
   means for generating an ultrasonic wave flux which is applied to the sample, whereby longitudinal and transverse ultrasonic waves travel in the sample; and
   lens means made of a medium allowing an ultrasonic wave flux to be transmitted therethrough, said lens means including a lens surface having first and second lens portions coupled to each other with a boundary therethrough, one of said lens portions being arranged for diverging one of said longitudinal and transverse ultrasonic waves traveling in the sample, and the other lens portion being arranged for housing the other or said longitudinal and transverse ultrasonic waves on a point in the sample, said first and said second lens portions being formed by different aspherical surfaces.

10. An apparatus according to claim 9, wherein said one lens portion comprises an acoustic absorbing member of a surface thereof.

* * * * *